US009867963B2

(12) United States Patent
Khalaj

(10) Patent No.: US 9,867,963 B2
(45) Date of Patent: Jan. 16, 2018

(54) NEEDLE HUB FOR OVER-THE-NEEDLE CATHETER

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 14/306,605

(22) Filed: Jun. 17, 2014

(65) Prior Publication Data

US 2015/0359999 A1 Dec. 17, 2015

(51) Int. Cl.
*A61M 5/178* (2006.01)
*A61M 25/00* (2006.01)
*A61M 25/06* (2006.01)
*A61B 5/00* (2006.01)
*A61N 1/05* (2006.01)

(52) U.S. Cl.
CPC ....... *A61M 25/0097* (2013.01); *A61B 5/4893* (2013.01); *A61M 25/0606* (2013.01); *A61B 5/6848* (2013.01); *A61N 1/0502* (2013.01); *A61N 1/0504* (2013.01); *A61N 1/0551* (2013.01)

(58) Field of Classification Search
CPC .......... A61M 25/0014; A61M 25/0097; A61M 25/06; A61M 25/0606; A61M 25/0612; A61M 25/0625; A61M 19/00; A61M 2205/054; A61N 1/0551; A61B 17/3401
USPC .......................... 604/164.01, 164.04, 164.07
See application file for complete search history.

(56) References Cited

U.S. PATENT DOCUMENTS

| | | | |
|---|---|---|---|
| 5,380,301 A | | 1/1995 | Prichard et al. |
| 5,976,110 A | * | 11/1999 | Greengrass ........ A61B 17/3401 604/158 |
| 6,363,273 B1 | * | 3/2002 | Mastrorio ......... A61M 25/0668 600/434 |
| 6,554,809 B2 | | 4/2003 | Aves |
| 6,814,725 B2 | | 11/2004 | Gutierrez |
| 2002/0198557 A1 | | 12/2002 | Freigang et al. |
| 2004/0073159 A1 | * | 4/2004 | Nelson .............. A61M 25/0606 604/21 |
| 2004/0186542 A1 | * | 9/2004 | van Venrooij ....... A61N 1/0529 607/116 |
| 2009/0012578 A1 | | 1/2009 | Carrez et al. |

(Continued)

FOREIGN PATENT DOCUMENTS

JP 2000-116791 4/2000

OTHER PUBLICATIONS

PCT Search Report, dated Sep. 7, 2015.

*Primary Examiner* — Emily Schmidt
(74) *Attorney, Agent, or Firm* — Dority & Manning, P.A.

(57) ABSTRACT

The present disclosure is directed to an over-the-needle (OTN) catheter assembly having an improved needle hub. The OTN catheter assembly includes a catheter defining a lumen extending from a proximal end to a distal end. A needle having a proximal end and a distal end is configured within the lumen of the catheter. The needle hub is configured with the proximal end of the needle and includes a bore defined therethrough. The needle hub also includes at least one cavity extending from the bore to an exterior surface of the needle hub. Thus, the needle extends at least partially through the bore of the needle hub such that the needle is exposed via the cavity from the exterior surface of the needle hub so as to engage a nerve stimulator apparatus.

18 Claims, 4 Drawing Sheets

(56) References Cited

U.S. PATENT DOCUMENTS

| | | | |
|---|---|---|---|
| 2009/0171304 A1* | 7/2009 | Cao | A61B 17/3478 604/272 |
| 2012/0059308 A1* | 3/2012 | Hsu | A61M 19/00 604/21 |
| 2012/0130269 A1* | 5/2012 | Rea | A61B 5/0488 600/554 |
| 2014/0025039 A1* | 1/2014 | Rajendran | A61B 17/3401 604/512 |

* cited by examiner

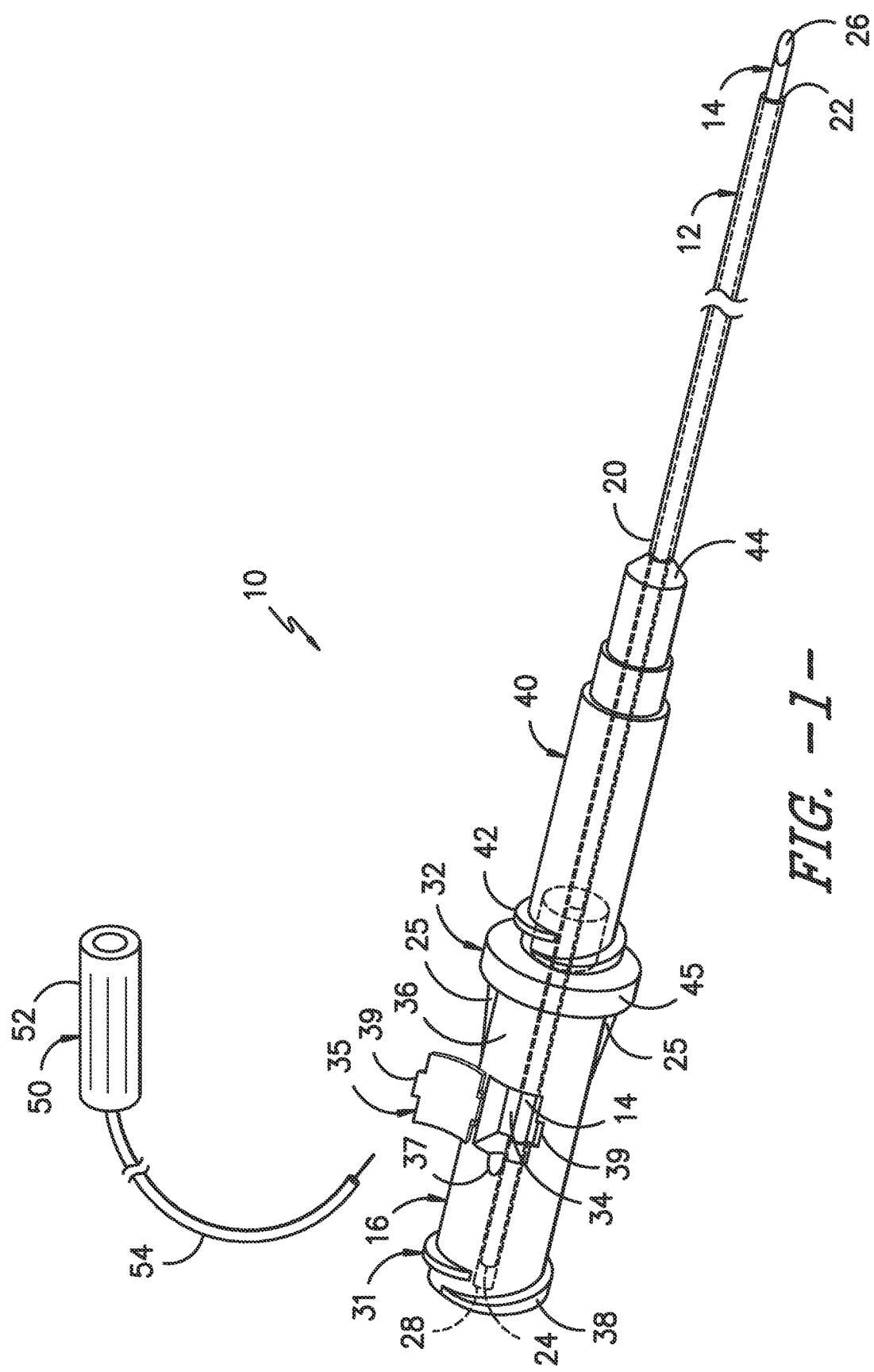
FIG. -1-

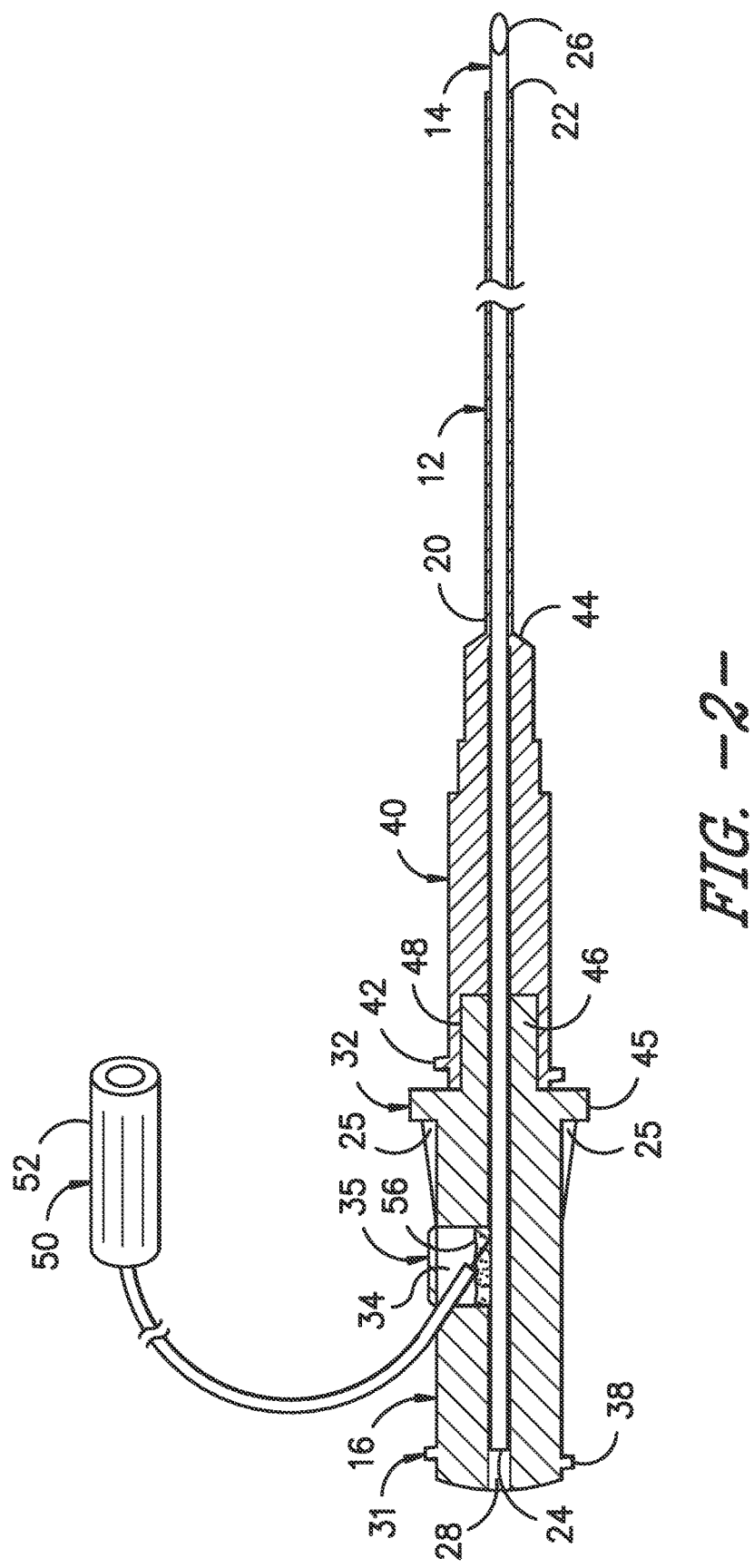
FIG. -2-

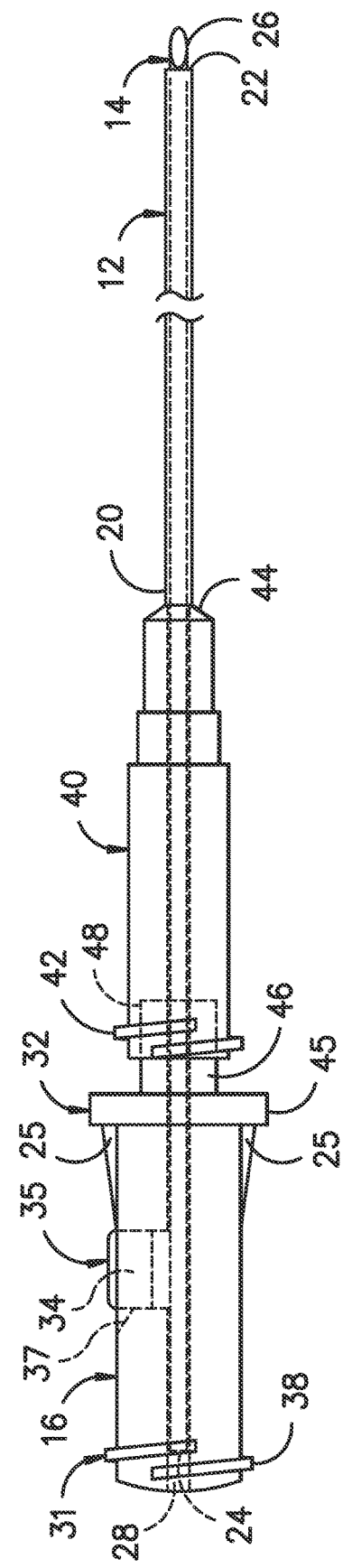
FIG. -3-

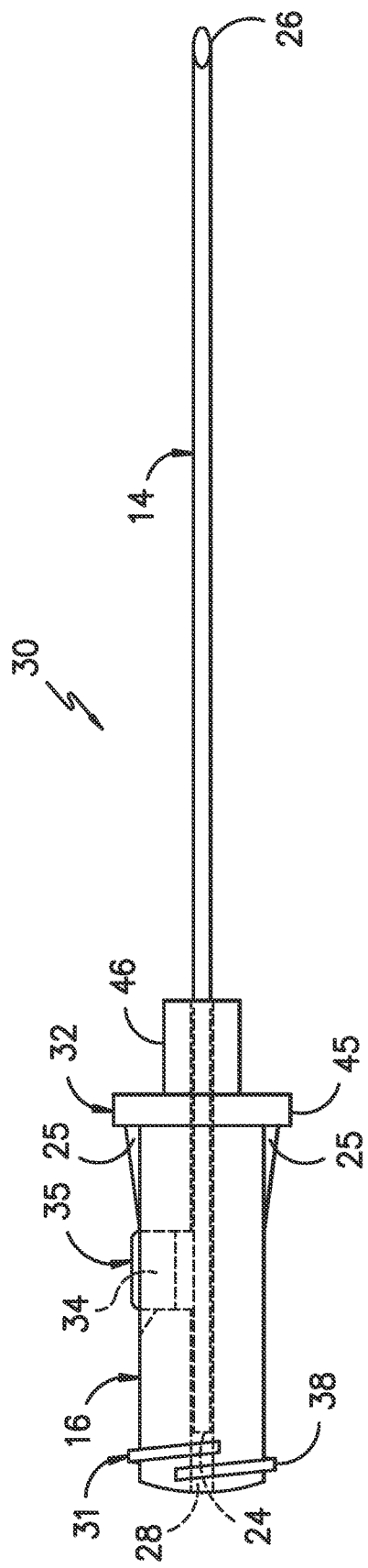
FIG. -4-
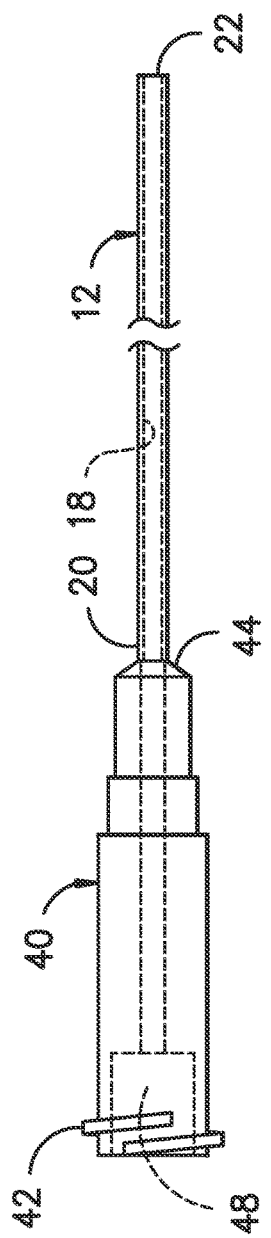
FIG. -5-

NEEDLE HUB FOR OVER-THE-NEEDLE CATHETER

FIELD OF THE INVENTION

The present invention relates generally to the field of medical catheters and more particularly to a needle hub for an over-the-needle (OTN) catheter.

BACKGROUND

Devices used to administer a fluid inside the anatomy of a patient are well known. For example, hypodermic needles, catheters, and the like are often used to deliver medication and other fluids to targeted sites within the body. In many instances, catheters are preferred because they can deliver fluid to a particular site over a period of time. Since catheters are generally made of a flexible plastic material, a needle is typically used to insert the catheter within a patient. For example, certain catheters, generally referred to as "through-the-needle" catheters, often require stiff, hollow introducer needles for placement within the anatomy. Thus, the catheter can be inserted through the needle after the needle is located at the targeted site. Typically, such introducer needles have sharp tips that may damage tissue and/or nerves during their delivery into a body, thus causing discomfort for the patient.

Another type of catheter, generally referred to as an "over-the-needle" (OTN) catheter, includes a catheter coaxially mounted onto a needle. In this type of catheter, the catheter and the needle may be inserted into a patient together. Once the catheter and the needle are located at the targeted site, the needle can be removed, leaving the catheter in place. Thus, OTN catheters can be purposely directed to an exact location without the need to thread the catheter within a patient. Accordingly, OTN catheters have gained increased attention in regard to delivering anesthetic medication, for example, for the purposes of nerve block.

For example, some regional anesthesia delivery techniques include placing an OTN catheter having a nerve stimulator needle into a patient near a nerve to be blocked and then advancing the needle until the target nerve is reached as determined by observing muscle contractions in response to the current flow through the stimulator needle. Such nerve stimulation assemblies require a special stimulator needle coupled with a stimulator wire that can be expensive to manufacture. In addition, many medical procedures require the use of an OTN catheter with and without stimulation, therefore, a physician may have to purchase multiple OTN catheters for a single medical procedure, thereby further increasing costs.

As such, the medical art is continuously seeking new and improved OTN catheters that address the aforementioned problems. Accordingly, the present invention is directed to an OTN catheter assembly having an improved needle hub that reduces manufacturing costs, yet still provides stimulation capability.

SUMMARY OF THE INVENTION

Objects and advantages of the invention will be set forth in part in the following description, or may be obvious from the description, or may be learned through practice of the invention.

In certain aspects, the present invention relates to an over-the-needle (OTN) catheter assembly having an improved needle hub. The OTN catheter assembly generally includes a catheter coaxially mounted over a needle. Further, the catheter defines a lumen extending from a proximal end to a distal end of the catheter. The needle is configured within the lumen of the catheter and also includes a proximal end and a distal end. The needle hub is configured with the proximal end of the needle and includes a bore defined therethrough from a proximal end to a distal end of the needle hub. The needle hub may be mounted to the needle in a variety of ways. For example, in one embodiment, the needle may be bonded within the needle hub using an adhesive. In another embodiment, the needle hub may be molded atop the needing during the manufacturing process. The needle hub also includes at least one cavity extending from the bore of the needle hub to an exterior surface thereof. Thus, the needle extends at least partially through the bore such that the needle is exposed via the cavity from the exterior surface of the needle hub. Accordingly, the needle hub is configured such that a nerve stimulator apparatus can engage the needle through the cavity of the needle hub.

In one embodiment, the distal end of the needle hub is configured with the proximal end of the needle and the proximal end of the needle hub includes a Luer connection configured to engage a fluid delivery device. In another embodiment, the catheter assembly also includes a catheter hub having a proximal end and a distal end. Thus, the distal end of the catheter hub may be configured with the proximal end of the catheter.

In addition, the catheter hub is configured to engage the needle hub. For example, in certain embodiments, the proximal end of the catheter hub may include a female component and the distal end of the needle hub may include a corresponding male component, wherein the female component is configured to receive the male component of the needle hub. Alternatively, the proximal end of the catheter hub may include a male component and the distal end of the needle hub may include a corresponding female component, wherein the female component is configured to receive the male component. Thus, in certain embodiments, the catheter hub may be configured to abut against a flange of the needle hub when the male and female components of the catheter hub and the needle hub are engaged.

In another embodiment, the catheter assembly may also include a nerve stimulator apparatus having a stimulator wire. Thus, in various embodiments, the stimulator wire may be configured to engage the needle through the cavity of the needle hub so as to provide stimulation to a targeted nerve site within a patient via the needle, e.g. to a nerve bundle. It should be understood by those of ordinary skill in the art that the cavity may be located at any suitable location along the length of the needle hub. For example, the cavity may be located at or near the distal end of the needle hub. Alternatively, the cavity may be located at or near the proximal end of the needle hub. In particular embodiments, the cavity may also include a conductive adhesive or epoxy configured therein so as to maintain contact between the stimulator wire and the needle during a medical procedure.

In still additional embodiments, the needle hub may also include a cap configured to secure the stimulator wire within the cavity such that the wire maintains contact with the needle. In addition, the cap may be configured to cover the cavity so as to prevent leakage from within the cavity. In certain embodiments, the cap may be a separately molded cap that can be attached to or snapped onto the needle hub. Alternatively, the cap may be integrally hinged with the needle hub. In further embodiments, the needle hub may also include one or more wing-like handles configured on the exterior surface of the needle hub. Thus, the wing-like handles are configured to assist a user with gripping the needle hub, e.g. during a medical procedure. It should also be understood that the needle hub may have any suitable shape. For example, in various embodiments, the needle hub may have a substantially cylindrical shape or a substantially rectangular shape.

In another aspect, the present invention relates to an improved needle assembly for an over-the-needle (OTN) catheter. The needle assembly includes a needle having a proximal end and distal end and a needle hub configured with the proximal end. Further, the needle is configured to fit within at least a portion of a lumen of a catheter. The needle hub has a bore defined therethrough from a proximal end to a distal end of the needle hub and includes at least one cavity extending from the bore to an exterior surface of the needle hub. Thus, the needle extends at least partially through the bore of the needle hub such that the needle is exposed via the cavity from the exterior surface of the needle hub. Accordingly, the needle hub is configured such that a nerve stimulator apparatus can engage the needle through the cavity of the needle hub. It should be understood by those of ordinary skill in the art that the needle assembly may further include any of the additional features described herein.

In further aspects, the present invention relates to an over-the-needle (OTN) catheter assembly. The OTN catheter assembly generally includes a catheter coaxially mounted over a needle. Further, the catheter defines a lumen extending from a proximal end to a distal end of the catheter. The needle is configured within the lumen of the catheter and also includes a proximal end and a distal end. The catheter assembly also includes a hub assembly having a catheter hub and a needle hub. The catheter hub is configured with the proximal end of the catheter and the needle hub is configured with the proximal end of the needle. Further, the hub assembly has a bore defined therethrough with the needle configured at least partially through the bore. The hub assembly also includes at least one cavity extending from the bore to an exterior surface of the hub assembly such that the needle is exposed via the cavity from the exterior surface of the hub assembly.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an OTN catheter assembly in accordance with aspects of the invention;

FIG. 2 illustrates a cross-sectional view of one embodiment of an OTN catheter assembly in accordance with aspects of the invention;

FIG. 3 illustrates a perspective view of one embodiment of an OTN catheter assembly in accordance with aspects of the invention, wherein a catheter hub is partially detached from the needle hub;

FIG. 4 illustrates a perspective view of one embodiment of a needle assembly in accordance with aspects of the invention; and FIG. 5 illustrates a perspective view of one embodiment of a catheter hub in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the catheter is the end oriented towards a catheter insertion site), and "proximal" refers to the opposite direction (e.g., the proximal end of the catheter is typically inserted into a catheter connector, which in turn is typically connected to a fluid delivery device).

Generally, the present disclosure is directed to an improved needle hub for an over-the-needle (OTN) catheter and an OTN catheter assembly having same. Thus, the needle hub of the present disclosure is particularly useful for delivering anesthetic medication to a nerve bundle within a patient to provide a nerve block during a medical procedure. For example, in various embodiments, the OTN catheter assembly includes a catheter that defines a lumen extending from a proximal end to a distal end of the catheter. The proximal end has a catheter hub attached thereto. The catheter hub is configured with the needle hub such that the needle fits within the lumen of the catheter. Further, the needle hub has a bore defined therethrough from the proximal end to the distal end and at least one cavity extending from the bore of the needle hub to an exterior surface of the needle hub. The needle extends at least partially through the bore such that the needle is exposed via the cavity from the exterior surface of the needle hub. Thus, the needle hub can be coupled with a nerve stimulator apparatus via the cavity. Accordingly, the OTN catheter assembly as described herein provides an economical, adaptable catheter that can be used with or without stimulation.

The OTN catheter assembly of the present disclosure provides various advantages not present in the prior art. For example, the needle hub can be manufactured (e.g. molded) as single part, rather than multiple parts, thereby reducing manufacturing costs. In addition, the cavity of the needle hub is configured to expose the needle such that a nerve stimulator apparatus can be easily coupled thereto. Thus, the OTN catheter assembly provides a simple-to-manufacture, economic needle and needle hub assembly that can be used with or without stimulation. Accordingly, the same OTN catheter assembly can be used for multiple medical procedures without increasing costs.

Referring now to the drawings, FIGS. 1-5 illustrate various embodiments of an over-the-needle (OTN) catheter assembly 10 having an improved needle hub 16 according to the present disclosure. More specifically, FIGS. 1 and 2 illustrate perspective and cross-sectional views, respectively, of one embodiment of the OTN catheter assembly 10; FIG. 3 illustrates the OTN catheter assembly 10 where a catheter hub is partially detached from the needle hub; and FIGS. 4 and 5 illustrate a separate needle assembly 30 and catheter hub 40 in accordance with aspects of the invention.

As shown, the OTN catheter assembly 10 includes catheter 12 coaxially mounted onto a needle 14. More specifically, the catheter 12 defines a lumen 18 extending from a proximal end 20 to a distal end 22 of the catheter 12. In addition, the proximal end 22 of the catheter 12 may include a catheter hub 40 configured thereon, which will be discussed in more detail below. The needle 14 is configured within the lumen 18 of the catheter 12 and also includes a proximal end 24 and a distal end 26. A needle hub 16 is configured with the proximal end 24 of the needle 14 and includes a bore 28 defined therethrough from a proximal end 31 to a distal end 32 of the needle hub 16. For example, as shown particularly in FIG. 2, the needle 14 fits within the bore 28 such that the needle 14 is mounted within the needle hub 16. In certain embodiments, the needle 14 and the bore 28 are sized such that the needle 14 is friction fit within the bore 28. In addition, the needle 14 may be further secured within the bore 28 of the needle hub 16 via an adhesive. In still further embodiments, the needle hub 16 may be molded over the needle 14. It should also be understood that the needle hub 16 may have any suitable shape. For example, as shown in the illustrated embodiments, the needle hub 16 has a substantially cylindrical shape. In further embodiments, the needle hub 16 may have any other suitable shape, including but not limited to, a rectangle, a square, or similar.

Referring particularly to FIGS. 1 and 4, the proximal end 31 of the needle hub 16 may also include a Luer connection, e.g. a Luer-lock fitting, for mating communication with a fluid delivery device (not shown). The fluid delivery device may be any suitable device known in the art, such as a pump, reservoir, syringe, or the like. Further, the needle hub 16 may have any other conventional configuration.

Referring specifically to FIGS. 1-4, the needle hub 16 also includes at least one cavity 34 that extends from the bore 28 to an exterior surface 36 of the needle hub 16. Thus, the needle 14 is configured to extend at least partially through the bore 28 of the needle hub 16 such that the needle 14 is exposed via the cavity 34 from the exterior surface 36 of the needle hub 16. It should be understood by those of ordinary skill in the art that the cavity 34 may be located at any suitable location along the length of the needle hub 16. For example, as shown, the cavity 34 may be located at or near the center of the needle hub 16. In further embodiments, the cavity 34 may be located at or near the distal end 32 of the needle hub 16, at or near the proximal end 31 of the needle hub 16, or at any other suitable location along the length of the needle hub 16.

In certain embodiments, the needle 14 may pass through the cavity 34 and bonded on both ends such that the cavity 34 is sealed off from any fluid that enters the needle hub 16 (e.g. medication from a fluid delivery device). Thus, fluids or contaminants within the cavity 34 cannot mix with fluids (e.g. medications) that are pumped through the OTN catheter and vice versa. In another embodiment, rather than bonding the needle 14 on both ends of the cavity 34, the needle hub 16 may be molded over the needle 14 such that the cavity 34 is sealed off from any fluid that enters the needle hub 16.

In additional embodiments, it should be understood that the needle hub 16 may include one cavity 34 (as shown) or a plurality of cavities such that the needle hub 16 can be coupled with a nerve stimulator apparatus 50 with one or more stimulator wires 54 or to accommodate different locations of the stimulator apparatus 50. In addition, the cavity 34 may have any suitable shape and/or size so as to accommodate stimulator wires 54 of varying sizes. For example, as shown in FIG. 1, the cavity 34 has a substantially rectangular shape.

As shown in FIGS. 1 and 2, the nerve stimulator apparatus 50 as described herein may include stimulator wire 54 coupled to a nerve stimulator 52 that provides a current through the stimulator wire 54. Thus, the stimulator wire 54 is configured to engage the needle 14 through the cavity 34 of the needle hub so as to provide stimulation to a targeted nerve site within a patient via the needle, e.g. to a nerve bundle. It should be understood, however, that the nerve stimulator apparatus 50 can further include any suitable components known in the art and the illustrated embodiment is provided for illustrative purposes only. In addition, as shown, the cavity 34 may also include a conductive adhesive 56 or epoxy configured therein so as to maintain contact between the stimulator wire 54 and the needle 14 during a medical procedure.

Referring back to FIG. 1, the needle hub 16 may also include a cap 35 configured to secure the stimulator wire 54 within the cavity 34 such that the stimulator wire 54 maintains contact with the needle 14. In additional embodiments, the cap 35 may be configured to cover the cavity 34 so as to prevent leakage from within the cavity 34. For example, in embodiments that contain a conductive adhesive 56 within the cavity 34, the cap 35 is configured to prevent the adhesive from exiting the cavity 34. In addition, as shown, the cap 35 may be shaped so as to correspond to the opening created by cavity 34. As such, in the illustrated embodiment, the cap 35 has a substantially rectangular shape. In certain embodiments, the cap 35 may be a separately molded cap that can be attached to the needle hub, e.g. by molded snaps and/or fasteners. In alternative embodiments, the cap 35 may be integral with the needle 16. Thus, in various embodiments, the cap 35 may be hinged with the needle hub 16 such that the cap 35 can rotate between an open and closed position. In still further embodiments, the cap 35 may include a locking component 39 (e.g. a latch) configured to secure the cap 35 in the closed position. It should be understood that the locking component 39 may be any suitable locking mechanism known in the art such that the cap 35 remains secured in the closed position (e.g. molded snaps, fasteners, Velcro, adhesive, etc.). The needle hub 16 may also include a cut-out 37 that is sized for the stimulator wire 54 to fit therethrough when the wire 34 is in contact with the needle 14 and the cap 35 is in the closed position.

Referring particularly to FIGS. 2-5, the catheter 12 may also include catheter hub 40 having a proximal end 42 and a distal end 44. Thus, the distal end 44 of the catheter hub 40 may be configured with the proximal end 20 of the catheter 12. In addition, as generally shown in the figures, the catheter hub 40 may be coupled with the needle hub 16 such that the catheter 12 is coaxially mounted onto the needle 14. More specifically, as shown particularly in FIGS. 2 and 5, the proximal end 42 of the catheter hub 40 may include a female component 48 and the distal end 32 of the needle hub 16 may include a corresponding male component 46, wherein the female component 48 is configured to receive the male component 46. Alternatively, the proximal end 42 of the catheter hub 40 may include a male component and the distal end 32 of the needle hub 16 may include a corresponding female component. In addition, in certain embodiments, the catheter hub 12 may be configured to abut against a flange 45 of the needle hub 16 when the male and female components 46, 48 are engaged.

In additional embodiments, the catheter hub 40 may also include a cavity that extends from a bore of the catheter hub 40 to an exterior surface of the catheter hub 40 (similar to the cavity 34 of the needle hub 60). Thus, the cavity of the catheter hub 40 is also configured to expose the needle 14 such that a nerve stimulator assembly 50 can be engaged therethrough. The cavity of the catheter hub 40 may further include any of the additional features described herein.

As mentioned, as user can choose to use the OTN catheter assembly 10 with or without the nerve stimulator apparatus 50 during use. For example, in one embodiment, the catheter assembly 10 can be used as a standard OTN catheter that simply delivers a treatment fluid from a fluid delivery device to a targeted site within a patient. In another embodiment, the user can begin the nerve block procedure by inserting the stimulator wire 54 of the nerve stimulator apparatus 50 into the cavity 34 of the needle hub 16 such that the wire 54 contacts the needle 14. In certain embodiments, the stimulator wire 54 may be secured in place via the cap 35 of the needle hub. The nerve stimulator apparatus 50 then transmits current from the stimulator connector 52 through the needle 14 to a targeted site within a patient.

In still additional embodiments, the needle hub 16 may also include one or more handles configured on the exterior surface 36 of the needle hub 16. For example, as shown in the illustrated embodiments, the needle hub 16 includes two wing-like handles 25 configured on exterior surface 36 of the needle hub 16. Thus, the wing-like handles 25 are configured to assist a user with gripping the needle hub 16 during use (e.g. when inserting the needle 14 within the catheter 12). In still further embodiments, the needle hub 16 may include any number of handles having any suitable shape, e.g. finger wings that are commonly used in the art.

It should also be understood that the needle hub 16 as described herein may be constructed of any suitable material. For example, in certain embodiments, the needle hub 16 may constructed of plastic, a polymeric material, or any other suitable material. More specifically, in various embodiments, the needle hub 16 may be constructed of thermoplastic, polyvinyl chloride (PVC), polyethylene, polypropylene, polyisoprene, polyurethane, and/or any other suitable material.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An over-the-needle (OTN) catheter assembly, comprising:
    a catheter comprising a proximal end and a distal end, said catheter defining a lumen extending from said proximal end to said distal end;
    a needle configured within the lumen of said catheter, said needle having a proximal end and a distal end;
    a stimulator wire configured to provide a current to said needle; and
    a needle hub configured with said proximal end of said needle, said needle hub comprising a bore defined therethrough from a proximal end to a distal end of said needle hub, said needle hub further comprising a flange and at least one open cavity proximal of said flange, the open cavity extending radially from said bore to an exterior surface of said needle hub, said needle extending longitudinally at least partially through said bore such that said needle is exposed to the exterior surface of said needle hub through said open cavity, said needle hub further comprising a cap comprising a first side and an opposing, second side, the first side secured to the exterior surface of said needle hub adjacent to said open cavity via a fixed hinge point, said second side being free, said second side of said cap being rotatable about the hinge point so as to move the cap between an open position and a closed position, said cap shaped to cover said open cavity and sit against the exterior surface of the needle hub in the closed position,
    wherein, when in the closed position, said cap secures said stimulator wire within said open cavity such that said stimulator wire maintains contact with said needle.

2. The catheter assembly of claim 1, wherein said distal end of said needle hub is configured with said proximal end of said needle, said proximal end of said needle hub comprising a Luer connection.

3. The catheter assembly of claim 1, further comprising a catheter hub having a proximal end and a distal end, said distal end of said catheter hub configured with said proximal end of said catheter.

4. The catheter assembly of claim 3, wherein said proximal end of said catheter hub further comprises a female component, and wherein said distal end of said needle hub further comprises a corresponding male component, wherein said female component is configured to receive said male component of said needle hub.

5. The catheter assembly of claim 4, wherein said catheter hub abuts against the flange of said needle hub when said male component of said needle hub is received with said female component of said catheter hub.

6. The catheter assembly of claim 1, wherein the stimulator wire is part of a nerve stimulator apparatus, wherein said nerve stimulator apparatus is configured to provide stimulation to a targeted nerve site within a patient via said needle.

7. The catheter assembly of claim 6, wherein said open cavity further comprises a conductive adhesive configured therein, said conductive adhesive configured to maintain contact between said stimulator wire and said needle.

8. The catheter assembly of claim 1, wherein said needle hub further comprises one or more wing-like handles configured on said exterior surface of said needle hub, said wing-like handles configured to assist a user with gripping said needle hub.

9. The catheter assembly of claim 1, wherein said needle hub comprises one of a cylindrical shape or a rectangular shape.

10. A needle assembly for an over-the-needle (OTN) catheter, said needle assembly comprising:
    a needle comprising a proximal end and a distal end, said needle configured to fit within at least a portion of a lumen of a catheter; and
    a needle hub configured with said proximal end of said needle, said needle hub comprising a bore defined therethrough from a proximal end to a distal end of said needle hub, said needle hub further comprising a flange and at least one open cavity proximal of said flange, the open cavity extending radially from said bore to an exterior surface of said needle hub, said needle extending longitudinally at least partially through said bore such that said needle is exposed to the exterior surface of said needle hub through said open cavity, said needle hub further comprising a cap comprising a first side and an opposing, second side, the first side secured to the exterior surface of said needle hub adjacent to said open cavity via a hinge point, said second side being free, said cap being rotatable about the hinge point so as to move between an open position and a closed position, said cap shaped to cover said open cavity and sit against the exterior surface of the needle hub in the closed position, wherein, when in the closed position, said cap is configured to secure a stimulator wire within said open cavity such that the stimulator wire maintains contact with said needle.

11. The needle assembly of claim 10, wherein said distal end of said needle hub is configured with said proximal end of said needle, said proximal end of said needle hub comprising a Luer connection.

12. The needle assembly of claim 10, wherein said distal end of said needle hub further comprises a male component configured to fit within a female component of a catheter hub.

13. The needle assembly of claim 12, wherein said catheter hub is configured to abut against the flange of said needle hub when said male component of said needle hub is received with said female component of said catheter hub.

14. The needle assembly of claim 10, wherein the stimulator wire is part of a nerve stimulator apparatus, wherein said nerve stimulator apparatus is configured to provide stimulation to a targeted nerve site within a patient via said needle.

15. The needle assembly of claim 14, wherein said open cavity further comprises a conductive adhesive configured therein, said conductive adhesive configured to maintain contact between said stimulator wire and said needle.

16. The needle assembly of claim 10, wherein said needle hub further comprises one or more wing-like handles configured on said exterior surface of said needle hub, said wing-like handles configured to assist a user with gripping said needle hub.

17. The needle assembly of claim 10, wherein said needle hub comprises one of a cylindrical shape or a rectangular shape.

18. An over-the-needle (OTN) catheter assembly, comprising:
- a catheter comprising a proximal end and a distal end, said catheter defining a lumen extending from said proximal end to said distal end;
- a needle configured within the lumen of said catheter, said needle having a proximal end and a distal end;
- a stimulator wire configured to provide a current to said needle; and
- a hub assembly comprising a catheter hub and a needle hub, said catheter hub configured with said proximal end of said catheter, said needle hub configured with said proximal end of said needle, said needle hub comprising a bore defined therethrough from a proximal end to a distal end of said needle hub, said needle hub further comprising a flange and at least one open cavity proximal of said flange, the open cavity extending radially from said bore to an exterior surface of said needle hub such that said needle is exposed to the exterior surface of said needle hub through said open cavity, said needle hub further comprising a cap comprising a first side and an opposing, second side, the first side secured to the exterior surface of said needle hub adjacent to said open cavity via a hinge point, said second side being free, said cap being rotatable about the hinge point so as to move between an open position and a closed position, said cap shaped to cover said open cavity and sit against the exterior surface of the needle hub in the closed position, wherein, when in the closed position, said cap secures said stimulator wire within said open cavity such that said stimulator wire maintains contact with said needle.

* * * * *